(12) United States Patent
Sturman

(10) Patent No.: US 7,710,127 B2
(45) Date of Patent: May 4, 2010

(54) TEST STRIP READER SYSTEM AND METHOD

(75) Inventor: Andy Sturman, San Diego, CA (US)

(73) Assignee: FCC, LLC, Boca Raton, FL (US)

( * ) Notice: Subject to any disclaimer, the term of this patent is extended or adjusted under 35 U.S.C. 154(b) by 109 days.

(21) Appl. No.: 11/995,105

(22) PCT Filed: Jul. 7, 2006

(86) PCT No.: PCT/US2006/026802

§ 371 (c)(1),
(2), (4) Date: Jul. 24, 2008

(87) PCT Pub. No.: WO2007/008842

PCT Pub. Date: Jan. 18, 2007

(65) Prior Publication Data

US 2009/0140753 A1    Jun. 4, 2009

Related U.S. Application Data

(60) Provisional application No. 60/697,765, filed on Jul. 8, 2005.

(51) Int. Cl.
*G01R 27/26* (2006.01)

(52) U.S. Cl. .................................. 324/663; 324/679
(58) Field of Classification Search ................ 324/663, 324/679
See application file for complete search history.

(56) References Cited

U.S. PATENT DOCUMENTS 5,336,467 A * 8/1994 Heidt et al. .............. 422/82.05
5,624,848 A    4/1997 Marnie et al.
6,448,064 B1   9/2002 Vo-Dinh et al.

* cited by examiner

*Primary Examiner*—Vincent Q Nguyen
(74) *Attorney, Agent, or Firm*—Bernard L. Kleinke; Duckor Spradling Metzger & Wynne

(57) ABSTRACT

A system and method is provided for reading a test strip by measuring the light intensity incident on a photodiode. The method may include reverse biasing the photodiode, measuring a time required to charge a capacitor using current generated by the photodiode, and using the time required to charge the capacitor to determine a condition of the test strip. The system may include a photodiode being reverse biased and a capacitor being charged by the reversed biased photodiode. The length of time to charge the capacitor may be proportional to the light intensity incident on the photodiode and may be used to determine a condition of the test strip.

26 Claims, 3 Drawing Sheets

TEST STRIP READER SYSTEM AND METHOD

RELATED APPLICATION

This application claims priority to U.S. provisional patent application, entitled TEST STRIP READER CIRCUIT AND FIRMWARE, Application. No. 60/697,765, filed Jul. 8, 2005.

FIELD OF THE INVENTION

The present invention relates in general to a system and method for reading a test strip, and more particularly relates to such a system and method for reading an assay test strip using a pair of photodiodes.

BACKGROUND ART

This section describes the background of the disclosed embodiment of the present invention. There is no intention, either express or implied, that the background art discussed in this section legally constitutes prior art.

Photodiodes are used in a variety of applications. One application is for reading assay test strips, which may be used for testing samples for pregnancy, drugs of abuse, tobacco, or others. The photodiodes detect light intensity changes or color changes on the test strip for detecting the presence or absence of a substance in the test sample.

A conventional way, for some applications, of measuring the light intensity incident on two photodiodes is to use a microcontroller with two analog to digital (A/D) channels. Amplifiers may be needed for each photodiode channel to convert their very low current into a voltage that the A/D can measure. This technique may employ a relatively large number of components and is expensive to manufacture. Also, under certain circumstances, the dynamic range of measurement may be limited by the number of bits in the A/D converter.

BRIEF DESCRIPTION OF THE DRAWINGS

The features of this invention and the manner of attaining them will become apparent, and the invention itself will be best understood by reference to the following description of certain embodiments of the invention taken in conjunction with the accompanying drawings, wherein.

CERTAIN EMBODIMENTS OF THE INVENTION

Figure 1:
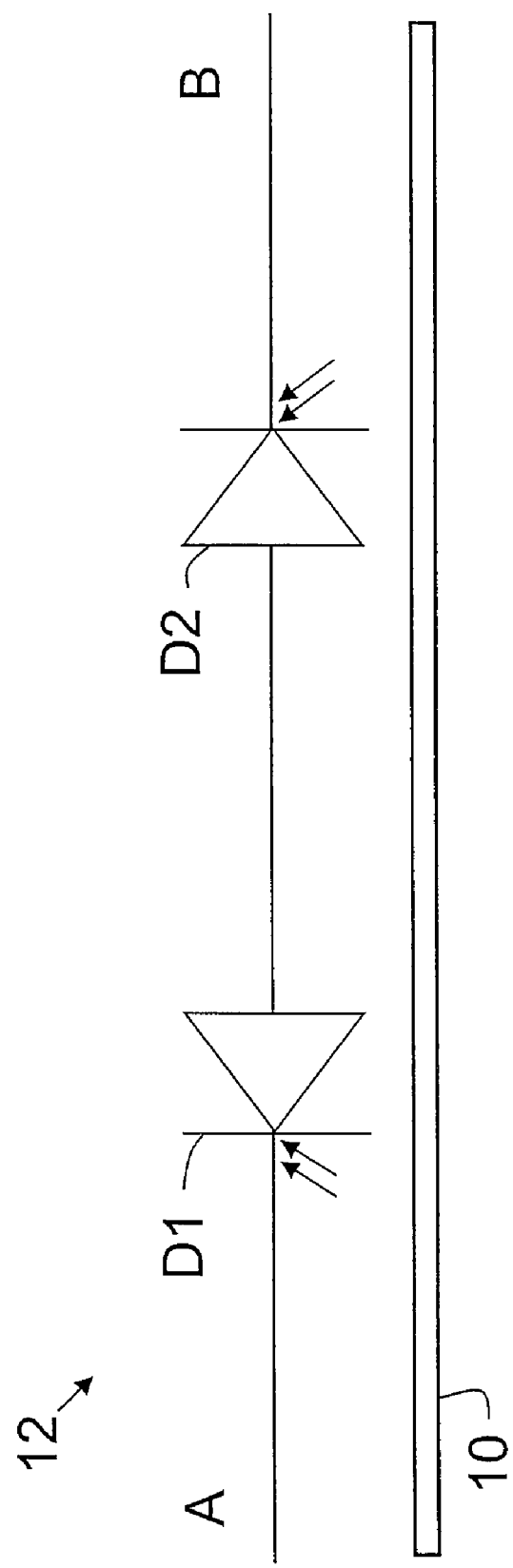
FIG. 1. is a greatly simplified schematic circuit diagram of a portion of a test strip reader system showing a pair of photodiodes configured in accordance with certain embodiments of the present invention.

It will be readily understood that the components of the embodiments as generally described and illustrated in the drawings herein, could be arranged and designed in a wide variety of different configurations. Thus, the following more detailed description of the embodiments of the system, components and method of the present invention, as represented in the drawings, is not intended to limit the scope of the invention, as claimed, but is merely representative of certain embodiments of the invention.

In accordance with certain disclosed embodiments of the present invention, there is provided a system and method for reading a test strip by measuring the light intensity incident on a pair of photodiodes. One embodiment of the disclosed system includes a pair of photodiodes, a timer, and a microcontroller. Another embodiment includes a pair of photodiodes, a plurality of inverters, a resistor, a capacitor, and a microcontroller.

An embodiment of the disclosed test strip reader system and method includes arranging a first photodiode and second photodiode in series and oppositely oriented, simultaneously forward biasing the first photodiode and reverse biasing the second photodiode, measuring a first current through the second photodiode, simultaneously forward biasing the second photodiode and reverse biasing the first photodiode, and measuring a second current through the first photodiode.

A system and method is disclosed which relates to the back biasing a photodiode and charging a capacitor to generate a pulse. The length of the pulse is proportional to the light intensity incident on the photodiode.

The embodiments of the present invention make use of the fact that a photodiode generates a very small current proportional to light intensity when it is reverse biased. The circuit shown in FIG. 1 forms the basis for this method. In the preferred embodiment, two photodiodes may be employed, but it should be understood that a single photodiode may also be employed.

As indicated in FIG. 1, a pair of photodiodes D1 and D2 are connected in series and oppositely poled back to back mounted adjacent a test strip 10 for a reader system 12. By changing the DC bias across points A and B, the current will either be proportional to the light hitting photodiodes D1 or D2. When a positive voltage is applied to point A relative to point B, then photodiode D1 is reverse biased, generating a current that is linearly proportional to the amount of light hitting it. This current passes through photodiode D2 because it is forward biased. If a positive voltage is applied to point B relative to point A then the reverse is true. The current through the circuit is linearly proportional to the amount of light hitting photodiode D2.

Figure 2:
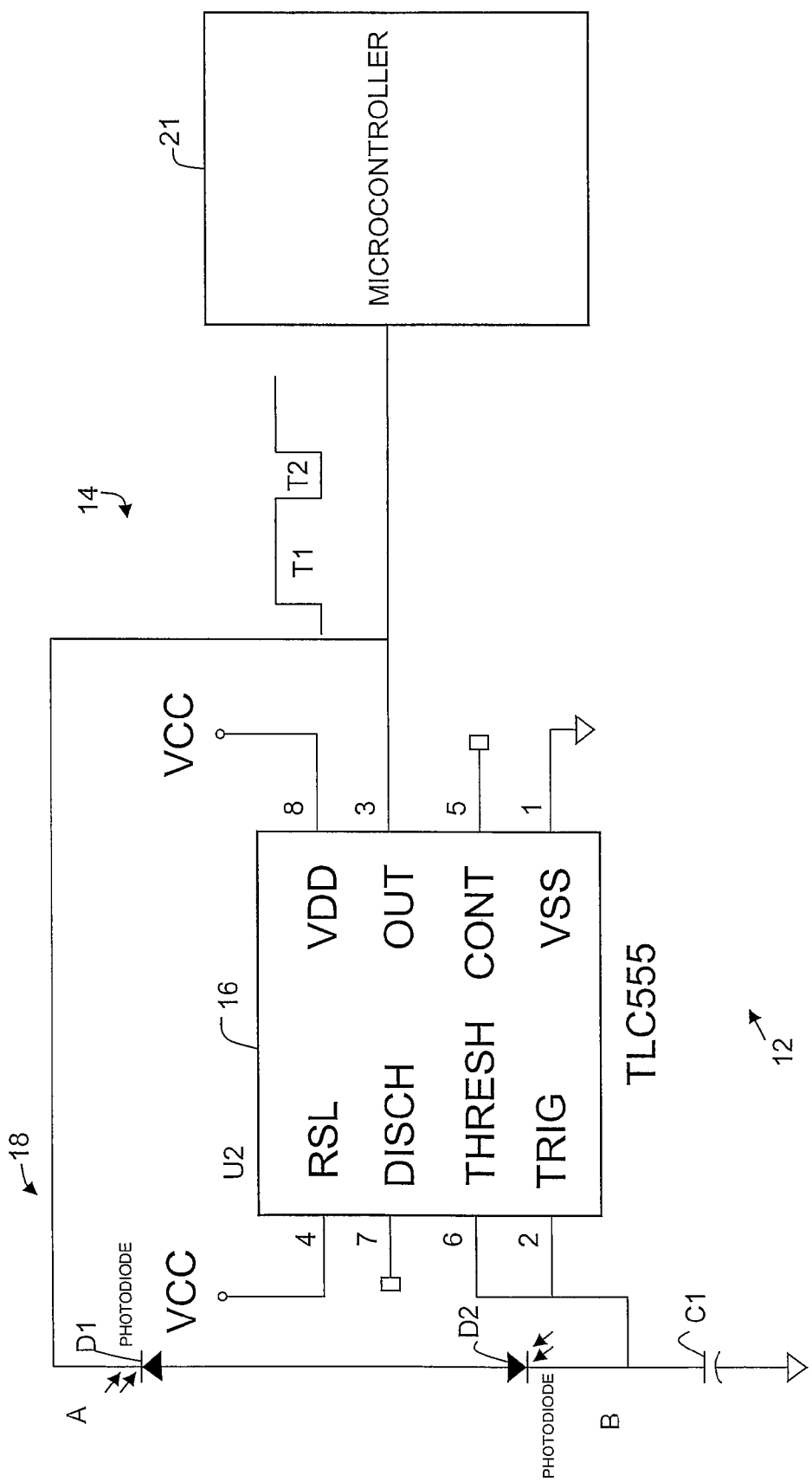
FIG. 2 is a schematic circuit diagram of the embodiment shown in FIG. 1.

If this combination is used in an oscillator circuit where the bias is alternating, then the output waveform has a shape that is dependent on the light intensity hitting each photodiode. A first embodiment of the disclosed system 12 is shown in FIG. 2 of an oscillator circuit 14 using a 555 timer chip 16. The oscillator circuit 14 includes a circuit 18 for reverse biasing the photodiodes D1 and D2.

When the output of the timer 16 (pin 3) is high, capacitor C1 gets charged up from the current generated by photodiode D1 because point A is at VCC and point B is at ⅓ VCC. The difference is ⅔ VCC. When the capacitor C1 voltage reaches ⅔ VCC, the output switches to 0 volts. Now point A is at 0 volts, point B is at ⅔ VCC and the difference is –⅔ VCC. In both cases, the bias voltage starts out at ⅔ VCC and drops to ⅓ VCC.

If we analyze the relationship between the light hitting photodiode D1 and the time T1, we get the following: Given $i$ is the current generated by photodiode D1 and is linear with the light intensity, and since $i=C*dv/dt$, the capacitance C is known, and dv is VCC/3, the equation for i becomes:

$i=K/dt$, where $K$ is a constant equal to $C*VCC/3$.

Therefore, t is inversely proportional to light intensity.

In the circuit of FIG. 2, time T1 is inversely proportional to the intensity of the light hitting photodiode D1 and time T2 is inversely proportional to the intensity of the light hitting photodiode D2.

With this circuit, only a single digital input pin of a microcontroller 21 is needed to measure both photodiodes D1 and D2. The microcontroller 21 may be from the PIC10F family of microcontrollers or other similar microcontrollers. Depending on the clock rate of the microcontroller 21 and the value of capacitor C1, a huge dynamic range of light levels can be measured compared to the A/D method. It is not as fast as the A/D method, but in many applications high conversion speed is not required.

Figure 3:
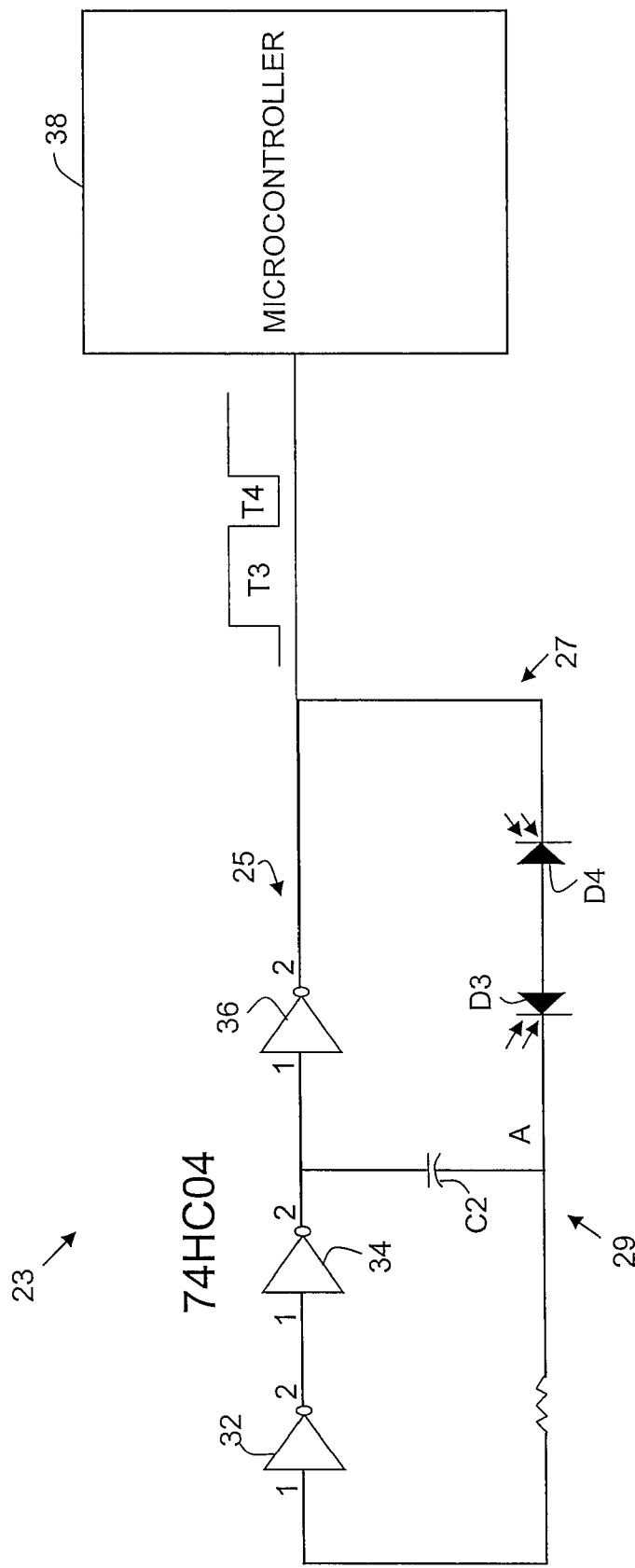
FIG. 3 is a schematic circuit diagram of another embodiment of the present invention.

Another embodiment of the disclosed system is shown in FIG. 3 of a reader system 23 using an oscillator circuit 25. The oscillator circuit 25 includes a circuit 27 for reverse biasing photodiodes D3 and D4. This circuit is a simple RC oscillator 29 using CMOS inverters, such as the 74HC04. The photodiodes D1 and D2 charge and discharge the capacitor Cal. 2 d depending on the state of the output. When the output is high, the current from photodiode D4 charges capacitor C2 until it reaches the high threshold of the inverter 32. The output then switches low and the current generated by photodiode D3 discharges capacitor C2 until it reaches the low threshold of the inverter 32. The output switches back to high and starts the process over again.

A microcontroller 38 may perform a count to determine the time the input to the microcontroller 38 is high, which is the time T3 for photodiode D3. The microcontroller 38 may perform a count to determine the time the input to the microcontroller 38 is low, which is the time T4 for photodiode D2. The microcontroller 38 may then use the times T3 and T4 to determine such things as wetness of the test strip and appearance of a test line.

Another advantage of these embodiments is that if times T1 and T2 or T3 and T4 are much longer than 16.6 msec, then 60 Hz noise tends to get cancelled out.

These circuits may not be especially good for measuring absolute light levels because of the tolerance in capacitors C1 and C2 and the input thresholds of the inverters. However, if the application software in the microcontroller is only concerned with percentage changes in light level, both circuits work very well.

While particular embodiments of the present invention have been disclosed, it is to be understood that various different modifications and combinations are possible and are contemplated within the true spirit and scope of the disclosed embodiments. There is no intention, therefore, of limitations to the exact disclosure herein presented.

What is claimed is:

1. A method of reading a test strip, comprising:
reverse biasing a photodiode;
measuring a time required to charge a capacitor using the current generated by the photodiode; and
using the time required to charge the capacitor to determine a condition of the test strip.

2. The method of claim 1, further comprising:
serially connecting a second photodiode to the photodiode, the photodiode and the second photodiode being oppositely oriented;
reverse biasing the second photodiode;
measuring a time required to discharge the capacitor using the current generated by the second photodiode; and
using the time required to discharge the capacitor to determine another condition of the test strip.

3. The method of claim 1, wherein the condition being determined is wetness of the test strip.

4. The method of claim 1, wherein the condition being determined is an appearance of a test line on the test strip.

5. The method of claim 1, wherein the reverse biasing the photodiode includes utilizing an oscillator circuit.

6. The method of claim 5, wherein the oscillator circuit includes a timer.

7. The method of claim 5, wherein the oscillator circuit includes an RC oscillator and at least one inverter.

8. The method of claim 5, wherein the measuring the time includes inputting an output of the oscillator circuit into a microcontroller.

9. The method of claim 1, wherein the time required to charge the capacitor is related to the intensity of light detected by the photodiode.

10. A system of reading a test strip, comprising:
means for reverse biasing a photodiode;
means for measuring a time required to charge a capacitor using the current generated by the photodiode; and
means for using the time required to charge the capacitor to determine a condition of the test strip.

11. The system of claim 10, further comprising:
means for serially connecting a second photodiode to the photodiode, the photodiode and the second photodiode being oppositely oriented;
means for reverse biasing the second photodiode;
means for measuring a time required to discharge the capacitor using the current generated by the second photodiode; and
means for using the time required to discharge the capacitor to determine another condition of the test strip.

12. The system of claim 10, wherein the condition being determined is wetness of the test strip.

13. The system of claim 10, wherein the condition being determined is an appearance of a test line on the test strip.

14. The system of claim 10, wherein the means for reverse biasing the photodiode includes an oscillator circuit.

15. The system of claim 14, wherein the oscillator circuit includes a timer.

16. The system of claim 14, wherein the oscillator circuit includes an RC oscillator and at least one inverter.

17. The system of claim 14, wherein the means for measuring the time includes means for inputting an output of the oscillator circuit into a microcontroller.

18. The system of claim 10, wherein the time required to charge the capacitor is related to the intensity of light detected by the photodiode.

19. A test strip reader, comprising:
a first photodiode;
a second photodiode serially connected to the first photodiode and oppositely oriented than the first photodiode;
an oscillator circuit utilizing the photodiodes and having an oscillating output related to the intensity of light at the photodiodes; and
a microcontroller using the oscillating output to determine at least one condition of a test strip.

20. The test strip reader of claim 19, wherein an anode of the first photodiode is electrically connected to an anode of the second photodiode.

21. The test strip reader of claim 19, wherein a cathode of the first photodiode is electrically connected to a cathode of the second photodiode.

22. The test strip reader of claim 19, wherein the oscillator circuit includes a timer.

23. The test strip reader of claim 19, wherein the oscillator circuit includes an RC oscillator using at least one inverter.

24. The test strip reader of claim 19, wherein the condition being determined is wetness of the test strip.

25. The test strip reader of claim 19, wherein the condition being determined is an appearance of a test line on the test strip.

26. A test strip reader system for reading a test strip, comprising:
   at least one photo diode;
   a capacitor connected to the photodiode;
   a circuit for reverse biasing the photodiode;
   a microprocessor for determining the time required to charge the capacitor using the current flowing through the reverse biased photodiode; and
   the microprocessor responding to the time determined to charge the capacitor for determining a condition of the test strip.

* * * * *